(12) United States Patent
Markelov

(10) Patent No.: US 6,395,560 B1
(45) Date of Patent: May 28, 2002

(54) HEADSPACE SAMPLING APPARATUS AND METHOD

(76) Inventor: Michael Markelov, 7276 Greenfield Trail, Chesterland, OH (US) 44026

( * ) Notice: Subject to any disclaimer, the term of this patent is extended or adjusted under 35 U.S.C. 154(b) by 0 days.

(21) Appl. No.: 09/365,679

(22) Filed: Aug. 2, 1999

(51) Int. Cl.$^7$ ................................................. G01N 1/22
(52) U.S. Cl. ........................ 436/181; 422/68.1; 422/83; 422/89; 436/54; 436/174; 73/23.2; 73/23.35; 73/23.41; 73/23.42
(58) Field of Search .............................. 422/78, 83, 93, 422/94, 68.1, 80, 89; 436/62, 68, 43, 49, 54, 138, 181, 174; 73/23.41, 23.42, 23.35, 863.11, 864.81; 95/89; 96/105

(56) References Cited

U.S. PATENT DOCUMENTS

| | | | | |
|---|---|---|---|---|
| 4,704,141 A | * | 11/1987 | Krebber | 55/197 |
| 5,417,924 A | * | 5/1995 | Di-Martino et al. | 422/101 |
| 5,441,700 A | * | 8/1995 | Markelov | 422/83 |
| 5,578,495 A | * | 11/1996 | Wilks | 436/178 |
| 5,827,944 A | * | 10/1998 | Nickerson | 73/23.41 |
| 5,866,072 A | * | 2/1999 | Bowe, Jr. et al. | 422/78 |
| 6,038,934 A | * | 3/2000 | Peterson | 73/863.86 |
| 6,076,410 A | * | 6/2000 | Renslow | 73/864.34 |
| 6,139,801 A | * | 10/2000 | Kawachi et al. | 422/88 |
| 6,146,895 A | * | 11/2000 | Green et al. | 436/47 |

* cited by examiner

Primary Examiner—Jill Warden
Assistant Examiner—Dwayne K. Handy
(74) Attorney, Agent, or Firm—Ralph E. Jocke; Daniel D. Wasil; Walker & Jocke

(57) ABSTRACT

A headspace sampling apparatus collects headspace vapor from a container holding a vapor phase and a non-vapor phase of a substance which is to be analyzed. The apparatus includes a dual needle apparatus (55). The dual needle apparatus is extended through a septum into a headspace portion (57) of a vial (58) holding the substance for analysis. A purge gas is supplied to a first fluid passage (54) in the dual needle. The purge gas sweeps the material in the headspace and passes the sample through a send fluid passage (56) in the needle. The extracted sample is selectively directed through a six port valve (76). In a first condition of the valve the sample is directed to a trap (80) for collection therein. After sample collection the condition of the six port valve is changed. Material is desorbed from the trap and directed through the valve into an analytical instrument (82). The ratios of the volumes occupied by liquid or solid phase of the substance and the vapor phase in the headspace of the vial is adjusted to selectively maximize sensitivity.

23 Claims, 5 Drawing Sheets

HEADSPACE SAMPLING APPARATUS AND METHOD

TECHNICAL FIELD

This invention relates to devices and methods of chemical analysis of materials. Specifically this invention relates to headspace analysis and apparatus and methods used to increase sensitivity in conducting such analysis.

BACKGROUND ART

Gas chromatography is one of the most powerful methods available for the separation of compounds for the purpose of purification, identification, and quantification. A volatile liquid sample is injected through a rubber septum into a heated glass injector port, which vaporizes the sample. The sample is swept through the column by an inert carrier gas. After passing through the column, the separated solutes flow through a detector the output of which is displayed on a recorder or computer. However, the samples that contain non-volatile constituents (polymers, dissolved salts, soils, biological matrices, etc.) cannot be directly introduced into a gas chromatograph. Such materials often require a tedious sample preparation procedure to remove non-volatile species.

One technique for delivering sample vapor to an analytical instrument is a 'purge and trap' apparatus. A purge and trap apparatus is used for capturing and identifying volatile organic compounds in a sample. Referring now to a purge and trap system, generally indicated 10, shown in FIG. 1, liquid or solid samples containing volatile organic compounds are sparged at a controlled temperature with a regulated flow of inert gas for a fixed period of time. Sparging gas enters through the needle adaptor 18 and passes through a sparging needle 12 which is inserted into a test tube containing a sample therein 14. The sparging needle 12 is adjusted so that the outlet is immersed in the sample. The sparging gas passes through the sample which produces a bubbling effect. Analytes stripped from the sample are accumulated and concentrated on a cool sorbent trap 24 comprised of a material suitable to collect the material to be accumulated in the application. The trap 24 functions as a sample concentrator which thermally traps and selectively later desorbs organic compounds for analysis by a gas chromatograph 30. Material which passes through the trap is initially directed to a vent 28 through a valve 26.

All analytes of interest are preferably completely transferred to the trap. Their quantification becomes ambiguous if this does not occur. This is associated with the fact that the vapor pressures in the bubbles depend on the radius of the bubble and the surface tension of the liquid (classical Kelvin Equation). Both vapor pressure and bubble radius are highly variable between samples. This is true even for materials such as environmental water samples which often contain salts, soaps or other materials. For these reasons the quantification of partially removed analytes becomes very difficult, and purge and trap procedures generally require intensive quality control to ensure that all analytes of interest are completely transferred to the trap. This limits the usefulness of the purge and trap approach for many volatile substances that are poorly removable from the matrix of substances included in the sample (alcohols in water for example). Often highly volatile materials are difficult to trap and material may be lost.

After the material of interest is accumulated in the trap 24, the trap 24 is then rapidly heated. The valve 26 is changed to fluidly connect a column of a gas chromatograph thereto. The analytes are desorbed from the trap as a plug and are moved by a flow of carrier gas which passes through a fitting 15, through the trap and valve, and into the gas chromatograph. The gas chromatograph provides an output indicative of the substances in the sample.

After passage of the sample to the gas chromatograph, the condition of valve 26 is again opened to vent 28. The trap is then baked above the desorption temperature so that water and heavier volatile chemicals that it is desirable not to introduce into the analytical instrument, are passed to vent 28. This clears the trap, reducing interference with subsequent reconcentration, separation, or detection of the analytes from other samples.

Further disadvantages of the conventional purge and trap apparatus are foaming during purge of the sample, contamination from the re-use of the sample holding container and safety hazards. Foaming of the sample during passage of the sparging gas results in net sample loss and less accuracy when calculating sample concentration. Re-use of the sample holding container increases the likelihood of contamination from prior samples. Contamination may result in incorrect sample concentration indications and may falsely indicate that certain chemicals are present in the sample, when actually these chemicals are left over from previous samples due to insufficient cleaning. Safety hazards may arise when the glass vial containing a sample shatters due to a possible pressure overload from sparge gas or other problem. Thus a safety shield is often needed to provide protection in the event of breakage.

Headspace technology is a relatively new technique which allows the sampling of the vapor phase of a sample for analysis in a gas chromatograph. This headspace sampling ensures that only volatile species that can be eluted from the column of the gas chromatograph will be introduced into the instrument. In headspace sampling a volatile non-vapor phase (liquid or solid) sample attains equilibrium with a vapor phase in a sealed vial. Equilibrium is established when the level of liquid in the vial no longer changes so that the total quantity of liquid and vapor remains constant. A syringe may be used to retrieve a small amount of vapor for analysis. Headspace technology is advantageous over conventional direct injection because it allows only vapor to enter the gas chromatograph. This eliminates the chance of contamination, or destruction of the instrument due to introduction of unevaporated sample. Since the sample is in the vapor form, sample volumes may be greater. Increased sample size generally results in increased sensitivity.

Samples of headspace vapor may be extracted from a sample vial using a number of other techniques. Such techniques often involve equilibrating the vapor and non-vapor phase of a substance for analysis within a closed vial. A sample needle is moved to pierce a septum on the vial such that a fluid passage through the needle is in fluid communication with the vapor phase of the sample in the headspace. To extract a headspace sample it is usually necessary to first pressurize the headspace with a suitable gas.

After the headspace has been pressurized, the pressure is released allowing the sample material to pass out of the vial and into an analytical instrument or other device. Examples of techniques for extracting sample vapor from a vial is shown in allowed U.S. patent application Ser. No. 09/131, 291) filed Aug. 10, 1998 the disclosure of which is incorporated by reference as if fully rewritten herein.

A drawback associated with conventional techniques for the extraction of a vapor sample from a headspace vial is that variations in pressure must be induced to extract the sample material. Such variations in pressure often affect the equilibrium between the vapor phase and the non-vapor phase of the substance being analyzed. Changes in equilibrium may change the makeup of the headspace vapor. Such changes which result from the sampling process often affect the results in ways that are undesirable.

Thus there exists a need for a headspace apparatus and method which reduces the disadvantages and limitations associated with prior art devices and methods.

OBJECTS OF INVENTION

It is an object of the present invention to provide a sampling apparatus that provides better sampling.

It is a further object of the present invention to provide a sampling apparatus that eliminates foaming associated with the purge and trap technique.

It is a further object of the present invention to provide a sampling apparatus with improved sensitivity which minimizes sample loss.

It is a further object of the present invention to provide a sampling apparatus which minimizes the risk of false readings due to contamination from prior samples.

It is a further object of the present invention to provide a sampling apparatus which includes two cooperative needles.

It is a further object of the present invention to provide a sampling apparatus which accomplishes a two-in-one function of purging and sweeping the headspace for retrieval of sample.

It is a further object of the present invention to provide a sampling apparatus which occupies less overall space than conventional purge and trap.

It is a further object of the present invention to provide a sampling apparatus which includes a dual needle for extracting sample vapor from a headspace in a vial.

It is a further object of the present invention to provide a sampling apparatus which reduces safety hazards and the potential shattering of sample containers.

It is a further object of the present invention to provide a sampling apparatus which utilizes a regular, inexpensive headspace vial as a disposable purge vessel.

It is a further object of the present invention to provide an improved method of sampling.

It is a further object of the present invention to provide a method of sampling that reduces the effects of pressure changes on the headspace sample.

It is a further object of the present invention to provide a method of sampling that achieves greater sample size.

It is a farther object of the present invention to provide a method of sampling which achieves increased sensitivity.

It is a further object of the present invention to provide an apparatus and method of sampling under conditions close to true thermodynamic equilibrium.

The foregoing objects are accomplished by a system and method of the present invention in which sample vapor is extracted from the headspace of a vial in which material to be analyzed is contained. Sample vapor is extracted from the headspace using a dual needle apparatus that in one exemplary embodiment includes two concentric overlaid sampling needle structures with two separate fluid passages: a first fluid passage and a second fluid passage. In other embodiments separate, parallel needles, each of which includes a fluid passage may be used.

Material to be analyzed is held in the vials generally in liquid or solid form. A headspace is maintained above the non-vapor phase of the material in each vial. The headspace contains a vapor phase of the substance to be analyzed. The non-vapor phase of the substance in the vial and the vapor phase of the substance in the headspace preferably achieves the equilibration between the condensed non-vapor phase and the vapor phase prior to sampling. The sample headspace vapor may be retrieved using the dual needle apparatus. Using one approach, a purge gas passes through one fluid passage in the needle into the headspace. The entering purge gas displaces the vapor from the substance to be analyzed in the headspace, and moves such material out of the headspace through the second passage in the dual needle. The sample headspace vapor is passed from the headspace through a six-port valve. The function of the six-port valve is to direct the sample headspace vapor extracted from the vial to various devices fluidly connected to the valve.

In one configuration of the apparatus the sample vapor extracted from the vial may be conducted directly to an analytical instrument. An example of such an instrument is a gas chromatograph. The pressure of the headspace is preferably maintained at the column pressure of the instrument to which the headspace vapor is conducted. This pressure remains generally balanced and may provide a greater sample size to achieve increased sensitivity.

In other configurations sample headspace vapors are passed through and collected on a cool sorbent trap or other trap device. Some vapor and purge gases pass through the trap without collection. Such gas and vapor pass through the six-port valve and are either discharged into the atmosphere through a vent or are otherwise processed or collected in a helium trap bake. The trap functions as a concentrator for material in the sample headspace vapor. After collection, the material from the sample headspace vapor is thermally desorbed off the trap by the activation of a trap heater or other release mechanism. The sample vapor is carried into an analytical instrument with the aid of a carrier gas. The instrument analyzes the material in the sample.

The system and method of the invention enables sweeping of the material in the headspace of the vial to maximize the collected volume of sample material from the headspace. The effects of pressure changes within the vial due to sampling are also reduced. The vapor sample is preferably obtained and delivered under conditions which maintain conditions close to thermodynamic equilibrium. The sensitivity of the system and method may also be selectively optimized for particular substances by controlling the ratios of headspace and sample volumes.

BEST MODES FOR CARRYING OUT INVENTION

Figure 1:
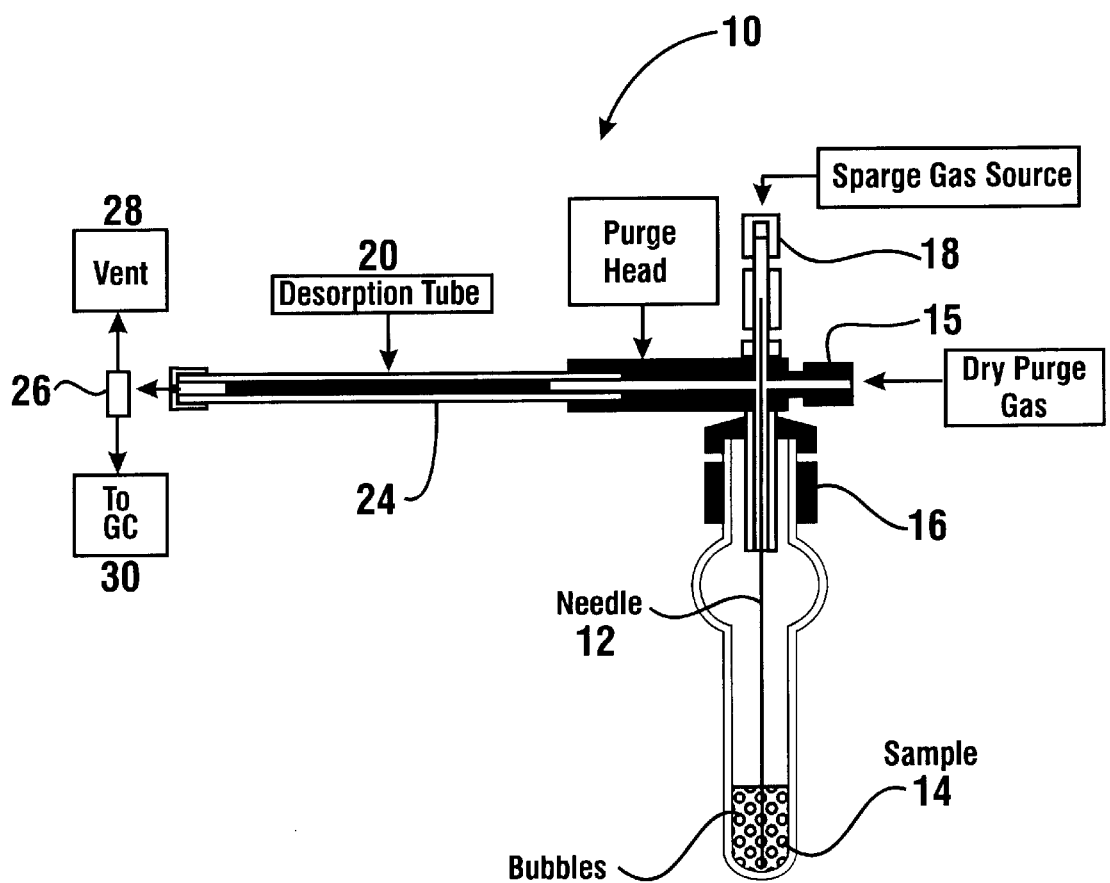
FIG. 1 is a schematic drawing of a conventional purge and trap design previously discussed.
Figure 2:
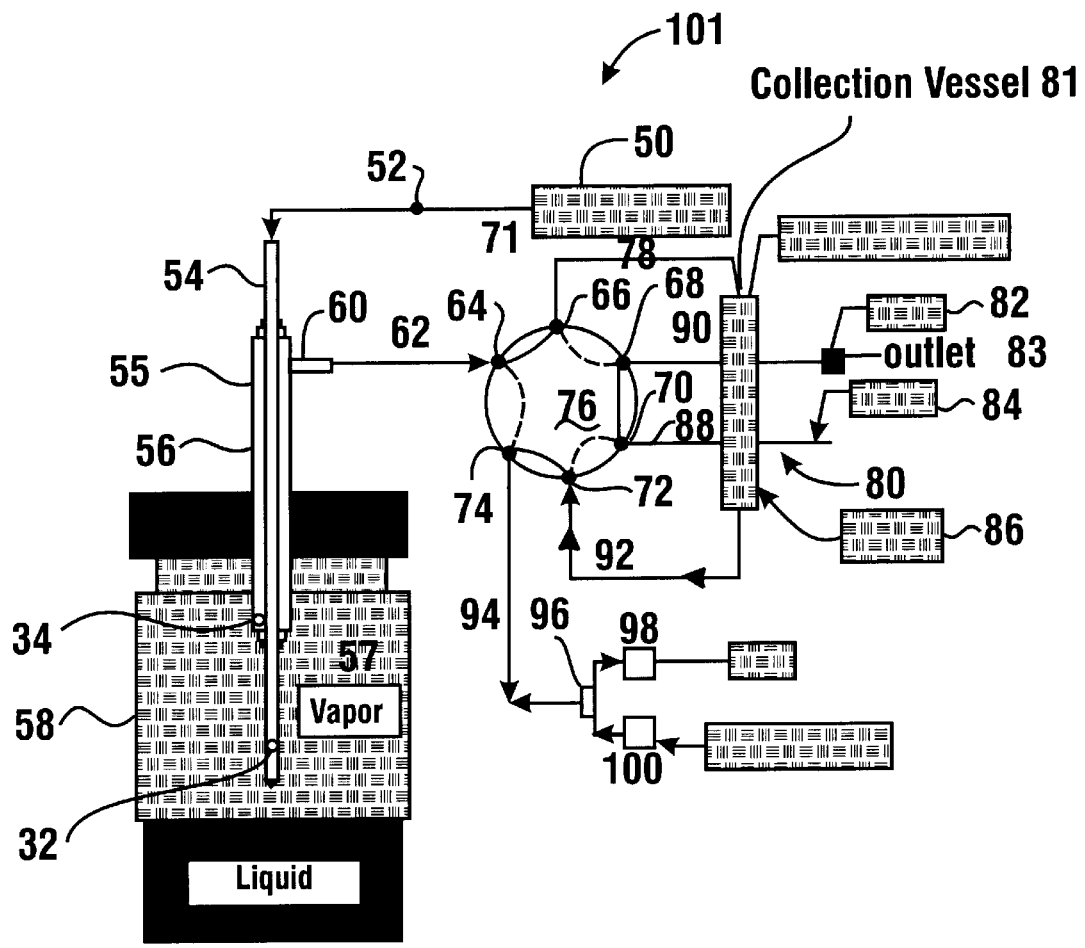
FIG. 2 is a schematic drawing of a headspace sampler apparatus when the valve is in a first condition.
Figure 3:
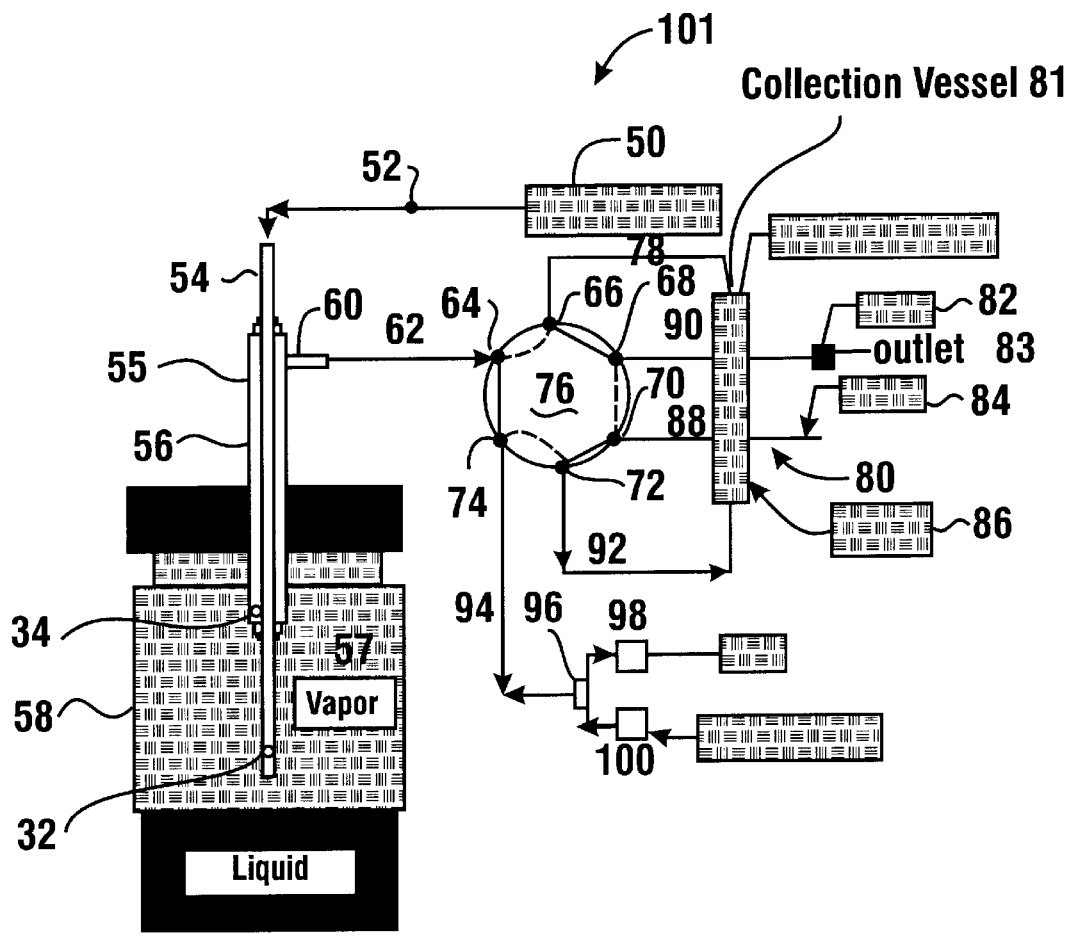
FIG. 3 is a schematic drawing of a headspace sampler apparatus when the valve is in a second condition.

Referring now to the drawings and particularly to FIGS. 2 and 3, there is shown therein a schematic view of one exemplary embodiment of a headspace sampler system of the present invention, generally indicated, 101. The system is adapted for sampling a substance located inside a vial 58. The vial in the exemplary embodiment is generally cylindrical and has an interior volume which defines a headspace 57 above the non-vapor phase of the substance therein.

The vial 58 utilized in the exemplary embodiment of the invention is a regular, inexpensive headspace vial which is commercially available. The vial generally contains a relatively small amount of the substance to be analyzed. The vials are sealed in the exemplary embodiment by installation of a Teflon® lined resilient septum comprised of silicone material. The septum is preferably installed and held in place in overlying relation of an opening to the vial by a cap, which is screwed or otherwise attached to an open top end of the vial. The sealed sample chamber prevents loss of sample during an equilibration process. The equilibration process may often be facilitated by heating the sample containing vial and by manipulating the vial to coat an interior wall surface with the sample material. This may be done using a mechanism which positions the vial horizontally and which rotates the vial to coat the interior wall surfaces thereof. In other embodiments other approaches to achieving equilibration may be used. After equilibration, the headspace vapors are extracted by a needle apparatus 55 in a manner later explained.

The system further includes a purge gas source 50. The purge gas is preferably an inert gas such as helium. As later explained the purge gas aids in headspace vapor retrieval by purging the sample. The described system further includes a trap 80 which functions to collect the sample material extracted from the headspace. In one exemplary embodiment, the trap includes a collection vessel 81 which is surrounded by a heater 86. The heater may be selectively activated to heat the collection vessel. Heating the collection vessel enables the sample material collected on the collection vessel to thermally desorb so it may be passed into an analytical instrument 82. In the described embodiment the analytical instrument may include a gas chromatograph. The gas chromatograph analyzes the material collected from the headspace vapor and delivers output data indicative of the components in the sample and/or the amounts thereof. In other embodiments other analytical instruments may be used.

The exemplary system further includes a carrier gas source 84. The choice of carrier gas will vary according to particular requirements of the system. In the case where the analytical instrument is a gas chromatograph, the carrier gas is selected for optimization of peak heights when the instrument displays the data collected when analysis takes place. The carrier gas functions to sweep the sample vapors through the analytical instrument which analyzes the sample material. The carrier gas serves to conduct the sample material when the material is thermally desorbed from the trap.

The system may further include a vent 98. The function of the vent is to allow unwanted gaseous materials to pass from the system and to achieve gas flow through the system components. The vent may be opened after the sample material has entered the analytical instrument. The vent may also be opened during the exchange of sample vials to purge unwanted materials from the lines.

The system of the exemplary embodiment further includes a helium trap bake 100. The trap bake is used to purge traps of unwanted materials and to ready the traps for reuse. Traps from which materials of interest have been desorbed may still contain residuals such as water and heavy volatiles. Connecting such traps in the trap bake 100 removes such materials by heating the trap to a sufficient temperature to liberate such materials. The materials may be vented through vent 98 to atmosphere or otherwise captured for treatment.

The exemplary system further includes a six-port valve 76. The valve may be selectively changed between two conditions. The first condition of the valve is shown schematically in FIG. 2 and the second condition is shown schematically in FIG. 3. In the first condition, the material in the headspace vapor is collected in the trap 80. The material which is not collected in the trap passes through the trap and is vented through a vent 98, or otherwise processed or collected. When the six port valve 76 is changed to a second condition shown in FIG. 3, the sample material collected in the trap may be liberated by thermal desorption or otherwise. Through the aid of a carrier gas 84, the sample material is passed into the analytical instrument 82. Also in this condition, the needle apparatus may be retracted from the vial so that it is possible to change samples.

In operation, the headspace sampler apparatus of the present invention operates to deliver gaseous samples to an inlet of a gas chromatograph or other analytical instrument. The apparatus and method achieves sampling generally under conditions of thermodynamic equilibrium. The material to be analyzed is placed within the sealed vial 58. The material is enabled or otherwise conditioned to equilibrate between the vapor phase portion and the liquid or solid non-vapor phase portion within the sealed vial. The needle apparatus 55 then pierces and extends through the septum on the top of vial 58 and enters the headspace portion 57 which holds the vapor phase portion of the material to be analyzed.

As schematically indicated in FIG. 2, the inert gas originates from the gas source 50. The gas enters line 52 and travels into an inlet to a first fluid passage 54 of the needle apparatus 55. The purge gas emerges from the first fluid passage through an opening 32 in the headspace area 57 of the vial. The purge gas flows into the headspace portion 57 of the vial and pushes the headspace vapor out of the vial through an opening 34 to a second fluid passage 56 of the needle apparatus 55. The sample headspace vapor then exits the second fluid passage 56 of the needle apparatus through an outlet 60. The sample vapor travels across a line 62 and into a port 64 of the six port valve 76.

The headspace vapor enters port 64 and exits through port 66 of six port valve 76. The headspace vapor travels across line 78 and onto the trap 80. In this condition the heater 86 which in the exemplary embodiment surrounds the trap, is turned off so that the material in the headspace vapor may collect on the cool trap 80. The purge gas and any other material not collected on the trap passes through the trap. Purge gas which passes through the trap travels across line 92 and enters port 72 of six port valve 76. The purge gas exits port 74 of valve 76 and travels across line 94 where it enters valve 96. The purge gas is vented to atmosphere through vent 98 or otherwise collected or treated.

In the exemplary embodiment, the gas source and the components which carry the sample material to the trap are maintained at generally the same temperature as the sample vapor within the vial. This achieves sample extraction generally under conditions approximating thermodynamic equilibrium. Such conditions are maintained through the dynamic sample removal activity which produces improved analytical results compared to other devices and sampling techniques.

The material collected from the headspace vapor in the trap 80 is analyzed by changing the six port valve 76 to the second condition represented in FIG. 3. In the second condition, sample material that has been collected in the trap 80 is directed to the analytical instrument 82. To liberate the sample material from the cool trap 80, the heater 86 is turned on, heating the trap. The heater heats the trap to a sufficient temperature so that the collected sample material of interest thermally desorbs from the trap. As the sample comes off the trap, the carrier gas from a source 84 moves the sample into the analytical instrument 82. After the sample has been expelled from the trap, the heater may be turned off through external controls or through programmable settings of a controller, computer or other control device.

It should be understood that the heating of the trap for purposes of liberating sample material is controlled so that materials which are not desired or which may be harmful to the analytical instrument remain in the trap. These materials may later be removed by placing in the trap bake 100. It should further be understood that while the described embodiment collects material in a cool trap and liberates material by heating the trap, other types of traps and other approaches to collection and liberation of sample materials may be used.

Figure 5:
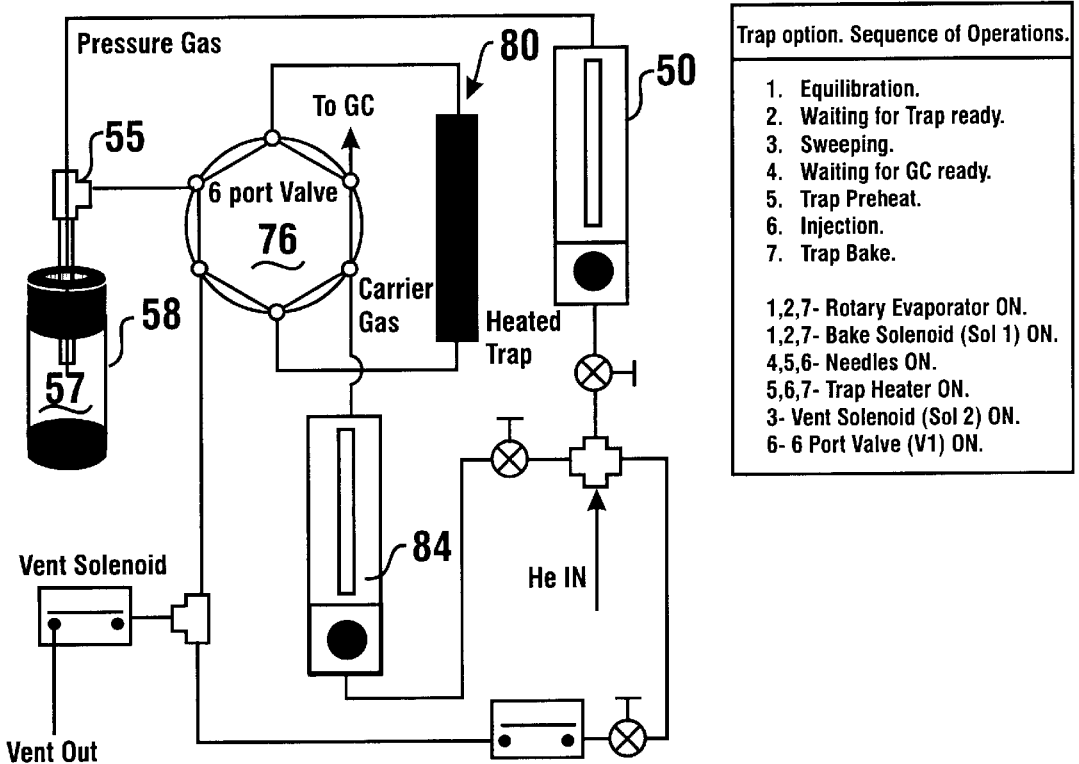
FIG. 5 is a schematic view of an alternative configuration of the dual needle system.

FIG. 5 shows another configuration for a system of the present invention in which sample material extracted from the headspace portion 57 of a sample vial 58 is concentrated in a trap 80. The sample material is later liberated from the trap for analysis with an analytical instrument.

The present invention may also be configured to conduct sampling and analysis using other procedures. For example, instead of sweeping headspace vapor from the vial into a trap, such vapor may be moved directly to the front of the column of a gas chromatograph or other analytical instrument. The headspace vapor flows through the instrument to a vent or other collection or treatment mechanism. This approach provides the sample material at the pressure of the analytical instrument. This provides balanced pressure between the headspace in the vial and the instrument. As is the case with the prior example when the material is collected in a trap for later analysis, the changes in pressure within the vial which can impact the makeup of the vapor sample is minimized. Likewise, the amount of the vapor sample extracted may be increased which may increase sensitivity. The sampling is preferably conducted generally under conditions of thermodynamic equilibrium.

The technique of using balanced pressure injection directly to the column of a gas chromatograph is difficult to achieve using other methods, especially for popular capillary megabore columns. The increased volume of sample vapors that may be achieved using the invention has been shown in many situations to achieve a tenfold increase in sensitivity. The present invention is especially useful in FET matrix independent methods where the matrix independence is achieved by use of small sample size, which may result in a loss in sensitivity. The dual needle approach may offset this loss and enables removal of analytes from the sample quantitatively.

Figure 4:
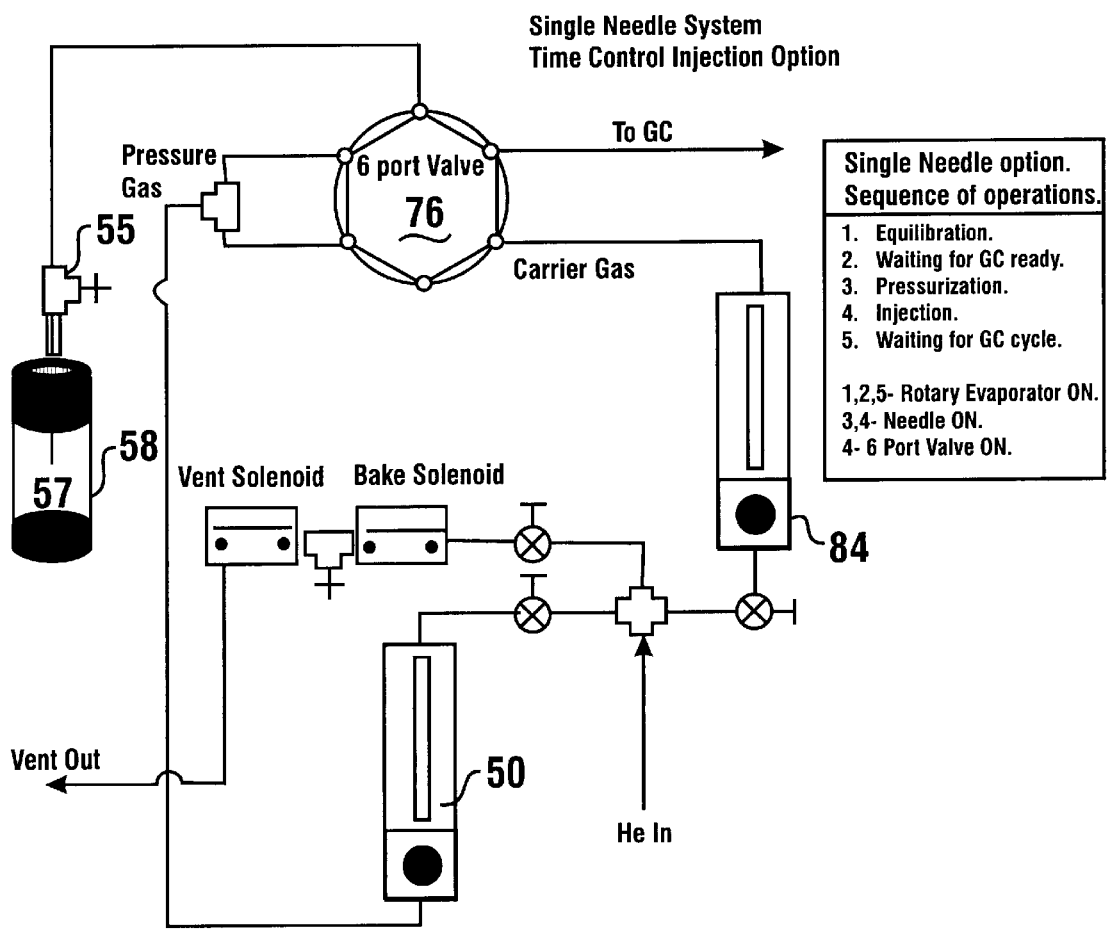
FIG. 4 is a schematic view of a system in which the dual needle system is used in a manner comparable to a single needle system.

Alternative forms of the present invention may also be configured to conduct more traditional headspace analysis techniques. This may be achieved by using only a single fluid passage in the needle to pressurize the headspace and extract sample vapor. This approach is comparable to conducting an analysis with a sample needle which has only a single fluid passage. This may be achieved by limiting movement of the dual needle into the headspace vials so that only opening 32 is in the headspace. Alternatively, the lines to one of the fluid passages in the dual needle may be plugged while the other is connected to provide pressurization and extraction through appropriate valving. An example of such a system is shown schematically in FIG. 4. Various alternating sampling approaches may be used depending on the analytical techniques to be used. In addition the exemplary embodiments shown may be used with techniques and/or the apparatus disclosed in co-pending allowed U.S. patent application Ser. No. 09/131,291 filed Aug. 10, 1998 the disclosure of which is incorporated by reference as if fully rewritten herein.

The headspace sampler apparatus of the present invention may be used to achieve several fundamental advantages over the prior art, particularly as a result of sampling the headspace with a needle apparatus including two separate fluid passages. First, the present invention eliminates the foaming problems associated with conventional purge and trap systems. Foaming of the sample during purge causes unnecessary sample loss because the foam tends to climb up onto the trap without first evaporating which may saturate the trap. Foaming may also result in collection of sample on the trap and which reflects the materials in the foam and suppresses other materials in the sample. Foaming also presents other potential ambiguities in the results.

A further advantage of the headspace sampler apparatus of the exemplary embodiment of the present invention is a reduction of the likelihood of instrument contamination since the needle apparatus only extracts the headspace vapors of the sample material. Contamination is much more likely using the prior art purge and trap techniques due to the possibility that unevaporated sample which was not properly collected could enter the gas chromatograph.

A further advantage of the headspace sampler apparatus of the present invention is that the technique of sweeping the headspace, which is achieved using the dual needle apparatus in the present invention, increases sensitivity because a larger amount of sample may be extracted from the headspace. The controlled pressure within the headspace vial may help to minimize the influence of sampling on the makeup of the sample. It may also be used to deliver a sample to an analytical instrument at a pressure suited to the instrument. The sampling under conditions approximating conditions of thermodynamic equilibrium, not attainable using other approaches, provides improved results.

The sensitivity of the system used with embodiments of the invention may also be selectively optimized for particular substances by controlling the ratios of headspace and sample volumes. This enables increasing the sensitivity of the headspace analysis technique for selected materials of interest in the sample. In regular, single needle type headspace analysis, a small aliquot of vapor sample is delivered to an analytical instrument. The sensitivity of such analysis is proportional to the equilibrium concentration of the analyte in the vapor phase above the condensed matrix. The equilibrium concentration can be expressed by the equation $$Cg=Co/(K+Vg/Vc)$$

where Cg is the equilibrium concentration of the analyte in the vapor phase

Co is the original concentration of the analyte in the sample

K is the partition coefficient

Vg is the volume of the vapor phase

Vc is the volume of the nonvapor phase

This equation is derived with the assumption that the change in the volume of the non-vapor phase of the sample (Vc) upon heating is small. The equation shows that the more sample taken for analysis, the smaller the volume ratio (Vg/Vc) and the higher the concentration of the analyte in the vapor phase (Cg). However, (Vc) cannot be increased indefinitely due to hardware restrictions.

When a dual needle system is used generally all the material in the headspace volume is removed. Therefore the sensitivity of the analysis is generally proportional to the total mass of the analyte in the vapor phase (Mg). Considering that the mass of the analyte in the vapor phase is equal to the product of the equilibrium concentration of the analyte in the vapor phase and the volume of the vapor phase is:

$$Mg = Cg \times Vg$$

The value of Mg can be expressed as follows:

$$Mg = Vg \times Co/(K + Vg/Vc)$$

It should be noted that in this equation expressing the mass of the analyte in the vapor phase extracted using the dual needle technique, Vg is present in both the numerator and denominator. The maxima for Mg were investigated by derivatizing with respect to Vg and equalizing the derivative to zero. This shows that the maximum for Mg is achieved at a definite ratio of the volumes of the vapor and non vapor phase. This is shown by the following equation $$Mg = Mg \text{ (max) when } Vg/Vc = K^{(0.5)}$$

or restated:

$$Vg/Vc = \sqrt{K}$$

corresponds to Mg (max)
Because the maximum mass of the analyte of interest is swept from the headspace at this volume ratio, sensitivity for this analyte is also maximized under these conditions.

This finding has been confirmed experimentally and shows that the technique of sweeping sample vapor from the headspace provides advantages over other sampling techniques. It also provides a user with a clear methodological approach to maximize sensitivity for a substance of interest by preparation of the samples to control the ratio of the volumes of the vapor phase and the non-vapor phase. This is achievable because the sample vapor is confined within a fixed volume of the sample vial.

The technique of maximizing sensitivity for selected substances, combined with the increased collection of sample vapor used in the exemplary embodiment of the present invention provides for improved sensitivity in the analysis using conventional analytical instruments.

It should be understood that while the embodiments shown employ a dual needle apparatus with coaxial needle structures, other multiple needle structures may be used. For example, it may be particularly desirable to use spaced multiple needles when sparging is desired or when a liquid sample is to be retrieved from the headspace vial. The methods and devices of the present invention may also be used in connection with techniques described in incorporated patent disclosure including the techniques used for increasing the surface area of the non-vapor phase of the sample to speed equilibration and to collect and deliver samples to analytical instruments.

Thus, the new headspace sampler apparatus and methods of the present invention achieves the above stated objectives, eliminates difficulties encountered in the use of prior devices and systems, solves problems and attains the desirable results described herein.

In the foregoing description certain terms have been used for brevity, clarity and understanding, however no unnecessary limitations are to be implied therefrom because such terms are for descriptive purposes and are intended to be broadly construed. Moreover, the descriptions and illustrations are by way of examples and the invention is not limited to the details shown and described.

In the following claims any element recited as a means for performing a function shall be construed as encompassing any and all means known to persons having skill in the art to be capable of performing the recited function, and shall not be deemed limited to the exemplary means shown herein as performing the function, or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations and relationships are set forth in the appended claims.

I claim:

1. A method comprising the steps of:
    (a) placing a non-vapor phase of a substance for analysis in an interior area of a vial;
    (b) sealing the interior area of the vial with a septum;
    (c) generating a vapor phase of the substance in a headspace of the interior area;
    (d) extending at least one sample needle through the septum, wherein the at least one sample needle includes a first fluid passage and a second fluid passage separate from the first fluid passage extending therethrough, and wherein the first fluid passage includes a first opening located in the headspace and the second fluid passage includes a second opening in the headspace;
    (e) introducing a gas into the headspace through the first fluid passage;
    (f) removing a sample of the vapor phase of the substance from the headspace through the second fluid passage.

2. The method according to claim 1 wherein the sample includes at least one material, and further comprising the step of:
    (g) introducing the material into an analytical instrument.

3. The method according to claim 1 wherein steps (e) and (f) are performed concurrently.

4. The method according to claim 1 and prior to step (e) further comprising the step of equilibrating the vapor phase and the non-vapor phase of the substance in the interior area.

5. The method according to claim 1 wherein in step (e) the gas introduced is an inert gas.

6. The method according to claim 4 wherein the equilibrating step includes transferring heat either to or from the substance in the vial.

7. The method according to claim 4 wherein the equilibrating step includes coating a wall portion bounding the interior area of the vial with the non-vapor phase of the substance.

8. The method according to claim 1 and wherein the sample includes at least one material, and further comprises the steps of:
    (g) collecting the material in a trap;
    (h) discharging at least a portion of the collected material from the trap;
    (i) delivering the material discharged from the trap to an analytical instrument.

9. The method according to claim 8 wherein step (g) comprises flowing the sample through the trap.

10. The method according to claim 8 wherein step (i) includes passing a gas through the trap, wherein the gas moves the material to the analytical instrument.

11. The method according to claim 10 wherein the analytical instrument includes a gas chromatograph having a column, and wherein the gas moves the material at a pressure in the column.

12. The method according to claim 8 wherein step (h) includes changing the temperature of the trap.

13. The method according to claim 12 wherein step (h) includes selectively heating the trap to discharge some but not all material collected therein.

14. The method according to claim 1 wherein in step (d) a single sample needle including both the first opening and the second opening thereon is extended in the headspace.

15. The method according to claim 1 wherein in step (d) a first needle including the first fluid passage thereon and a second including the second fluid passage thereon are extended in the headspace.

16. The method according to claim 1 wherein in step (f) the sample is removed responsive to introduction of the gas into the headspace in step (e) whereby the sample is displaced from the headspace.

17. The method according to claim 1 and further comprising the step of passing the vapor sample to an analytical instrument.

18. The method according to claim 1 wherein in step (a) an amount of the non-vapor phase of the substance placed in the interior area is controlled to generally maximize mass of an analyte included in the vapor phase of the substance removed in step (f).

19. The method according to claim 18 wherein the amount of the non-vapor phase of the substance placed in the interior area of the vial occupies a first volume (Vc), and wherein the interior area not occupied by the non-vapor phase of the substance occupies a second volume (Vg), and wherein after placing the non-vapor phase of the substance in the vial in step (a), the ratio of (Vg) to (Vc) is generally equal to the square root of a partition coefficient for the analyte.

20. The method according to claim 1 wherein step (d) includes extending the first opening into the headspace further than the second opening.

21. A method comprising the steps of:
(a) placing a non-vapor phase of a substance for analysis in an interior area of a vial;
(b) sealing the interior area of the vial with a septum;
(c) generating a vapor phase of the substance in a headspace of the interior area;
(d) equilibrating the vapor phase and the non-vapor phase of the substance in the interior area;
(e) extending a sample needle through the septum, wherein the sample needle includes a first fluid passage and a second fluid passage separate from the first fluid passage extending therethrough, and wherein the first fluid passage includes a first opening located in the headspace and the second fluid passage includes a second opening located in the headspace;
(f) subsequent to step (d), introducing an inert gas into the headspace through the first opening;
(g) removing a sample of the vapor phase of the substance from the headspace through the second opening, wherein the sample is removed concurrently with the introduction of the gas into the headspace in step (f), whereby the sample is displaced from the headspace by the gas.

22. The method according to claim 21 wherein in step (e) the first opening is extended further into the headspace than the second opening.

23. The method according to claim 21 wherein the amount of the non-vapor phase occupies a first volume (Vc), and wherein the amount of the vapor phase occupies a second volume (Vg), and wherein prior to step (f), the ratio of (Vg) to (Vc) is generally equal to the square root of the total mass of an analyte included in the vapor phase, whereby the amount of the non-vapor phase of the substance is controlled to generally maximize mass of the analyte removed in step (g).

* * * * *